(12) United States Patent
Yakubovsky et al.

(10) Patent No.: US 8,126,537 B2
(45) Date of Patent: Feb. 28, 2012

(54) METHOD AND APPARATUS FOR A MULTI-MODALITY IMAGING SYSTEM

(75) Inventors: Leonid Yakubovsky, Kiriat Bialik (IL); Alexander Vaisburd, Haifa (IL); Yaron Hefetz, Herzeliya (IL)

(73) Assignee: General Electric Company, Schenectady, NY (US)

( * ) Notice: Subject to any disclaimer, the term of this patent is extended or adjusted under 35 U.S.C. 154(b) by 1184 days.

(21) Appl. No.: 11/051,226

(22) Filed: Feb. 4, 2005

(65) Prior Publication Data
US 2006/0241408 A1    Oct. 26, 2006

(51) Int. Cl.
*A61B 5/05* (2006.01)
*A47B 23/06* (2006.01)

(52) U.S. Cl. .............................. 600/427; 600/425; 5/601

(58) Field of Classification Search .................. 600/415, 600/407, 425, 427, 436; 378/20, 208, 209; 5/47, 601, 611
See application file for complete search history.

(56) References Cited

U.S. PATENT DOCUMENTS

| | | | |
|---|---|---|---|
| 4,449,262 A | 5/1984 | Jahsman et al. | |
| 4,558,847 A | 12/1985 | Coates | |
| 4,613,122 A * | 9/1986 | Manabe | 5/601 |
| 4,984,774 A * | 1/1991 | Zupancic et al. | 5/601 |
| 5,590,429 A * | 1/1997 | Boomgaarden et al. | 5/600 |
| 5,953,776 A | 9/1999 | Sanders et al. | |
| 6,211,523 B1 | 4/2001 | Gagnon | |
| 6,242,743 B1 | 6/2001 | DeVito et al. | |
| 6,302,579 B1 * | 10/2001 | Meyer et al. | 378/196 |
| 6,399,951 B1 | 6/2002 | Paulus et al. | |
| 6,449,331 B1 | 9/2002 | Nutt et al. | |
| 6,456,684 B1 * | 9/2002 | Mun et al. | 378/20 |
| 6,516,478 B2 | 2/2003 | Cook et al. | |
| 6,574,808 B1 | 6/2003 | Brown et al. | |
| 6,614,871 B1 | 9/2003 | Kobiki et al. | |
| 6,615,428 B1 | 9/2003 | Pattee | |
| 6,640,363 B1 | 11/2003 | Pattee et al. | |
| 6,670,614 B1 | 12/2003 | Plut et al. | |
| 6,720,812 B2 | 4/2004 | Tumer et al. | |
| 6,729,263 B2 | 5/2004 | Miale et al. | |
| 6,955,464 B1 * | 10/2005 | Tybinkowski et al. | 378/209 |
| 7,024,710 B2 * | 4/2006 | Izuhara | 5/601 |
| 7,043,784 B2 * | 5/2006 | Plannerer | 5/601 |
| 7,065,813 B2 * | 6/2006 | Hoth et al. | 5/601 |

(Continued)

FOREIGN PATENT DOCUMENTS
JP    2000-102529    4/2000

*Primary Examiner* — Long V. Le
*Assistant Examiner* — Angela M Hoffa
(74) *Attorney, Agent, or Firm* — The Small Patent Law Group; Dean D. Small (57) ABSTRACT

An apparatus for examining a patient is provided. The apparatus includes a top plate, at least one top rail slideably coupled to said top plate, said top plate selectively positionable between a first imaging position and a second imaging position along an examination axis, a support member coupled to said at least one top rail, said support member configured to selectively change a position of said top plate along an axis perpendicular to said examination axis, said support member comprises at least one guide pin slideably coupled to said at least one rail during movement of said support member, said guide pin configured to retain said support member to said at least one top rail when said top rail is moved between a first modality position and a second modality position.

2 Claims, 6 Drawing Sheets

U.S. PATENT DOCUMENTS

| | | | |
|---|---|---|---|
| 7,292,673 B2 * | 11/2007 | Kroner et al. | 378/20 |
| 2002/0104163 A1 * | 8/2002 | Reimann | 5/601 |
| 2003/0105397 A1 | 6/2003 | Tumer et al. | |
| 2003/0128801 A1 | 7/2003 | Eisenberg et al. | |
| 2004/0200001 A1 * | 10/2004 | Stolze et al. | 5/601 |
| 2004/0261176 A1 * | 12/2004 | Plannerer | 5/601 |
| 2004/0261177 A1 * | 12/2004 | Hoth et al. | 5/601 |
| 2005/0023471 A1 | 2/2005 | Wang et al. | |
| 2005/0082487 A1 * | 4/2005 | Amano | 250/363.03 |

* cited by examiner

METHOD AND APPARATUS FOR A MULTI-MODALITY IMAGING SYSTEM

BACKGROUND OF THE INVENTION

This invention relates generally to imaging and treatment systems, and more particularly to methods and apparatus for aligning an object being scanned in multi-modality systems.

At least some multi-modality imaging and treatment systems are capable of using a combination of different modalities, such as, for example, Positron Emission Tomography (PET), Single Positron emission tomography (SPECT), Ultrasound, Magnetic Resonance Imaging (MRI), Computed Tomography (CT), Static X-Ray imaging, Dynamic (Fluoroscopy) X-Ray imaging, and radio-therapy. In a multi-modality system (sometimes referred to as a multi-modal system), a portion of the imaging hardware is utilized to perform different scans or treatments, (e.g., an image produced by SPECT is processed and displayed respectively, by the same computer and display, as an image produced by CT). However, the data acquisition systems (also referred to as an "imaging assembly") may be different. For example, on a CT/SPECT system, a radiation source and a radiation detector are used in combination to acquire CT data, while a radiopharmaceutical is typically employed in combination with a SPECT camera to acquire SPECT data.

In multi-modality systems, such as, for example, an integrated SPECT/CT system there may be an inherent registration of the SPECT and CT images the system acquires. Because the patient lies motionless on the same table during the SPECT and CT portions of the acquisition, the patient may be in a consistent position and orientation during the two acquisitions, greatly simplifying the process of correlating and combining the CT and SPECT images. This allows the CT image to be used to provide attenuation correction information for the reconstruction of the SPECT image, and allows an image reader to easily correlate the anatomic information presented in the CT image and the functional information presented in the SPECT image.

This inherent registration assumes an alignment of the SPECT and CT detector coordinate systems, or at least a known spatial transformation between the two coordinate systems. A misalignment of the coordinate systems may directly result in a misregistration of the images. Misregistration results not only in inaccurate localization, but also to incorrect attenuation correction of the functional image.

Proper SPECT and CT image registration may also require an alignment of the axial (z) axis of the SPECT and CT coordinate systems not only with each other, but also with the travel axis of the table that transports the patient between and during the SPECT and CT acquisitions. A co-axial SPECT/CT or other multi-modality system, especially for whole body scans, requires a relatively long axial travel distance to permit both imaging modalities the ability to image the region of interest. However, a patient table and table support may not be able to accommodate the alignment requirements while supporting a patient cantilevered out from the table support during an examination due to the extreme length of travel the patient table must travel to reach both imaging assemblies. For example, a co-axial imaging assembly arrangement requires a relatively long rail system, and the length of the bed may induce bending thereof, such that the patient position may change between the two imaging stations, even if the patient remains absolutely stationary.

A hospital suite may be space-limited and multiple modality systems require typically more floor space than a single-modality imaging unit. Additionally, patients preparing for the diagnostic imaging procedure must be loaded onto the table prior to the procedure, and unloaded from the table subsequent to the procedure. This loading and unloading can be difficult and uncomfortable for a patient who may have suffered recent trauma. Finally, the patient must be rigidly and accurately positioned and supported between imaging modalities and during each imaging procedure.

BRIEF DESCRIPTION OF THE INVENTION

In one embodiment an apparatus for examining a patient is provided. The apparatus includes a top plate, at least one top rail slideably coupled to the top plate, the top plate selectively positionable between a first imaging position and a second imaging position along an examination axis, a support member coupled to the at least one top rail, the support member configured to selectively change a position of the top plate along an axis perpendicular to the examination axis, the support member comprises at least one guide pin slideably coupled to the at least one rail during movement of the support member, the guide pin configured to retain the support member to the at least one top rail when the top rail is moved between a first modality position and a second modality position.

In another embodiment, an imaging system is provided. The imaging system includes a first and a second imaging assembly for obtaining medical diagnostic images of a patient for at least first and second imaging modalities, said imaging assemblies being substantially aligned along an examination axis, and a stretcher for supporting an object to be imaged, said stretcher positionable along said examination axis, said stretcher slideably coupled to a top plate, said top plate positionable in a first imaging modality position; said top plate positionable in a second imaging modality position.

In another embodiment a method of examining a patient is provided, the method comprises positioning a top plate in a first modality position, positioning the stretcher axially at a first imaging modality position, imaging the patient using a first imaging modality, positioning the top plate axially at a second imaging modality position, and imaging the patient using a second imaging modality.

DETAILED DESCRIPTION OF THE INVENTION

Figure 1:
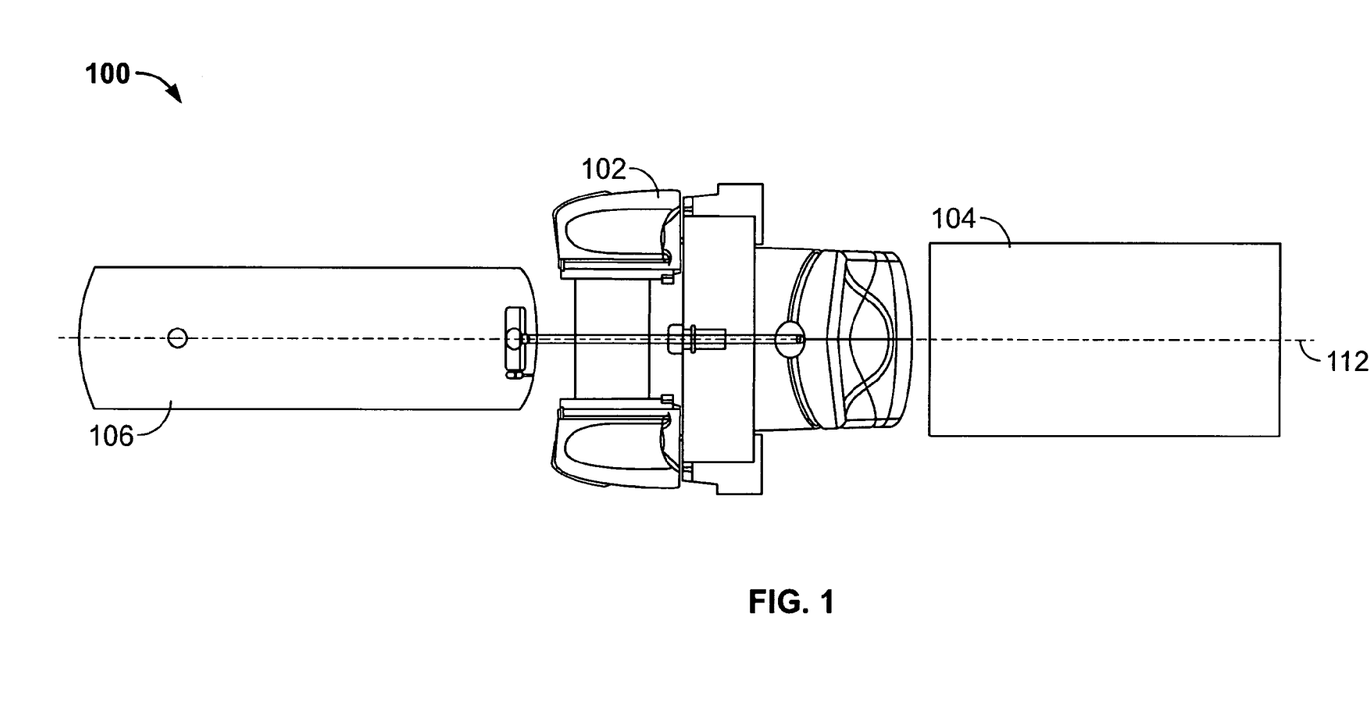
FIG. 1 is a schematic illustration of an imaging system containing both a first and a second imaging system aligned along the same imaging axis.

FIG. 1 is a schematic illustration of an exemplary embodiment of an imaging system 100. Imaging system 100 includes a first imaging assembly 102, a second imaging assembly 104, a patient table assembly 106, and a support mechanism (not shown). In the exemplary embodiment, imaging assembly 102 includes an associated examination axis 112, which defines the imaging axis of the first and the second imaging systems. As used herein, the examination axis is referenced to a single axis used to image the patient in both imaging systems. Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, a NM imaging assembly, and an ultrasound imaging assembly. Imaging assemblies 102 and 104 are aligned along the same examination axis 112.

Figure 2:
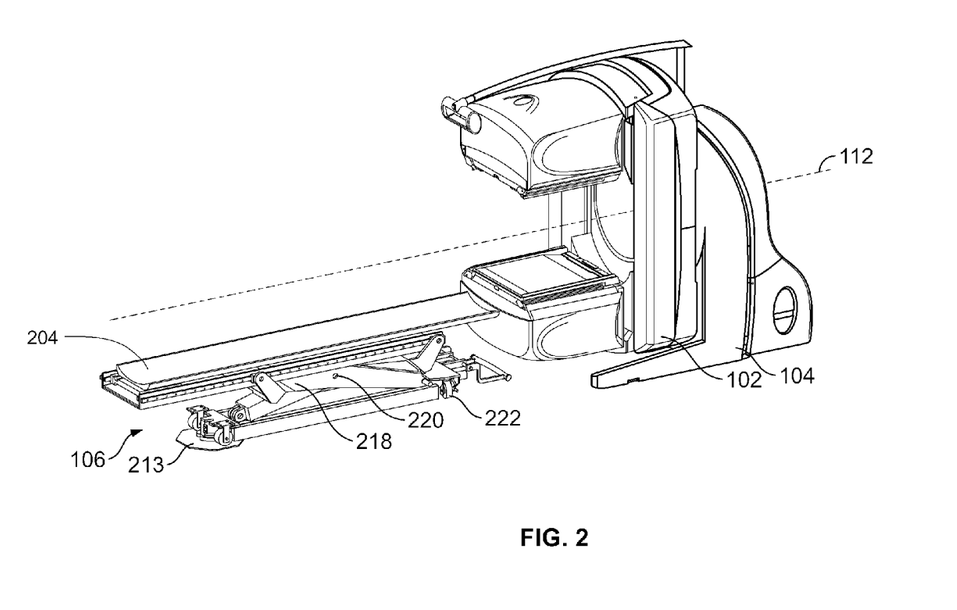
FIG. 2 is an exemplary embodiment of a patient table support mechanism, in fully retracted position, that may be used with the imaging system shown in FIG. 1.

FIG. 2 illustrates an exemplary embodiment of patient table assembly 106, in retracted mode, prior to positional alignment of the patient table assembly 106 with examination axis 112. Scissors legs 218, which pivot about pivot pin 220, are fully retracted as illustrated in FIG. 2. Stretcher 204 is positioned optionally at an elevation best suited for patient loading to ensure patient comfort. Stretcher 204 is illustrated in its lowest elevational position but may be positioned at any elevation over its range of vertical travel for patient loading. The center of table assembly pivot 213 is positioned substantially below examination axis 112. Table assembly pivot 213 enables table assembly 106 to pivot away from examination axis 112 in order to load a patient onto stretcher 204. Pivoting motion of table assembly 106 is facilitated by rolling elements 222, which pivot about a vertical axis and enable the operator to pivot the table assembly 106. Patient loading may occur during alignment of table assembly 106 with examination axis 112, or patient loading may occur with table assembly 106 positioned at an angle to examination axis 112, depending on the preference of the operator and/or the patient.

Figure 3:
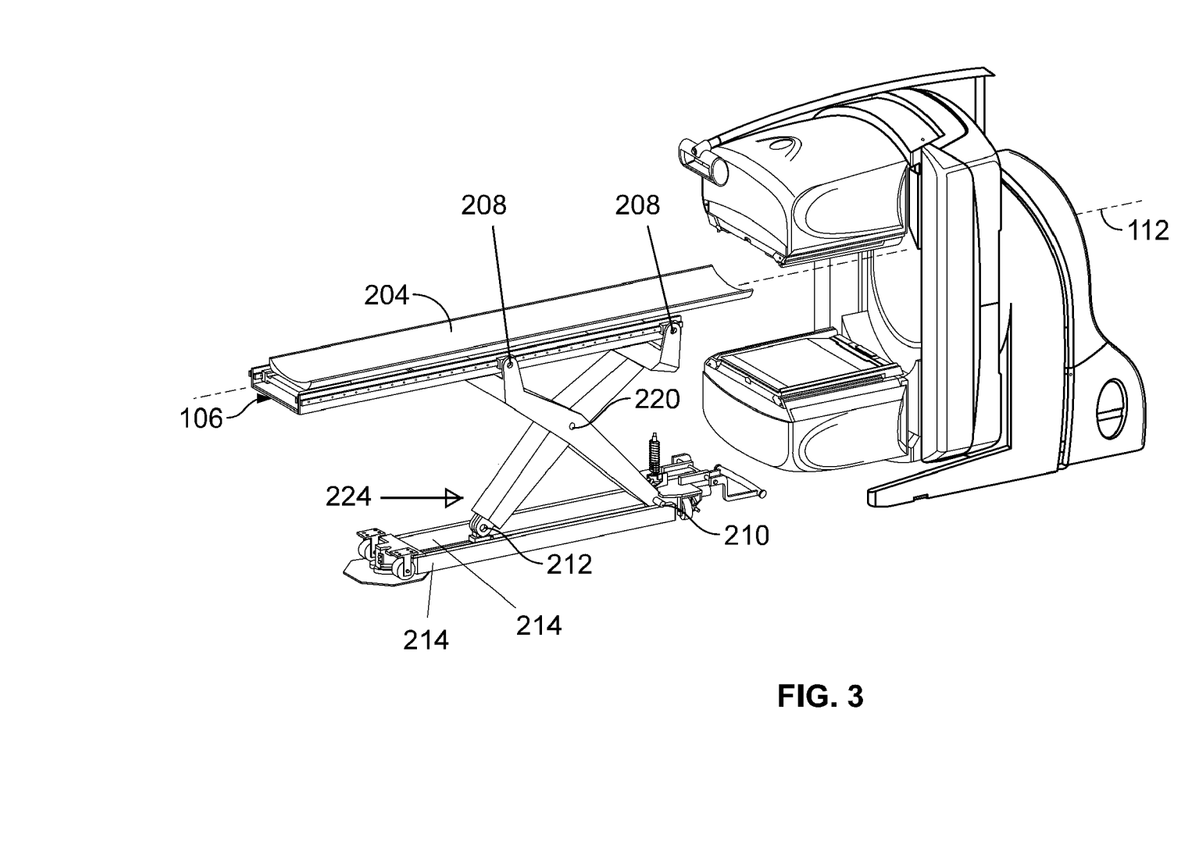
FIG. 3 is the patient table of FIG. 2, in elevated position, ready for extension into the imaging region.

FIG. 3 illustrates a position of table assembly 106 wherein a patient (not shown), positioned on stretcher 204, is substantially aligned with examination axis 112. Table assembly 106 is elevated by application of force 224 against slide pin 212. Slide pin 212 is slideably engaged with bottom rails 214 to enable axial motion of slide pin 212. Pivot pin 210 retains the assembly from moving axially during application of force 224, hence raising the table by scissors action and pivoting about pivot pin 210 and pivot pin 220, and sliding along guide pins 208.

Figure 4:
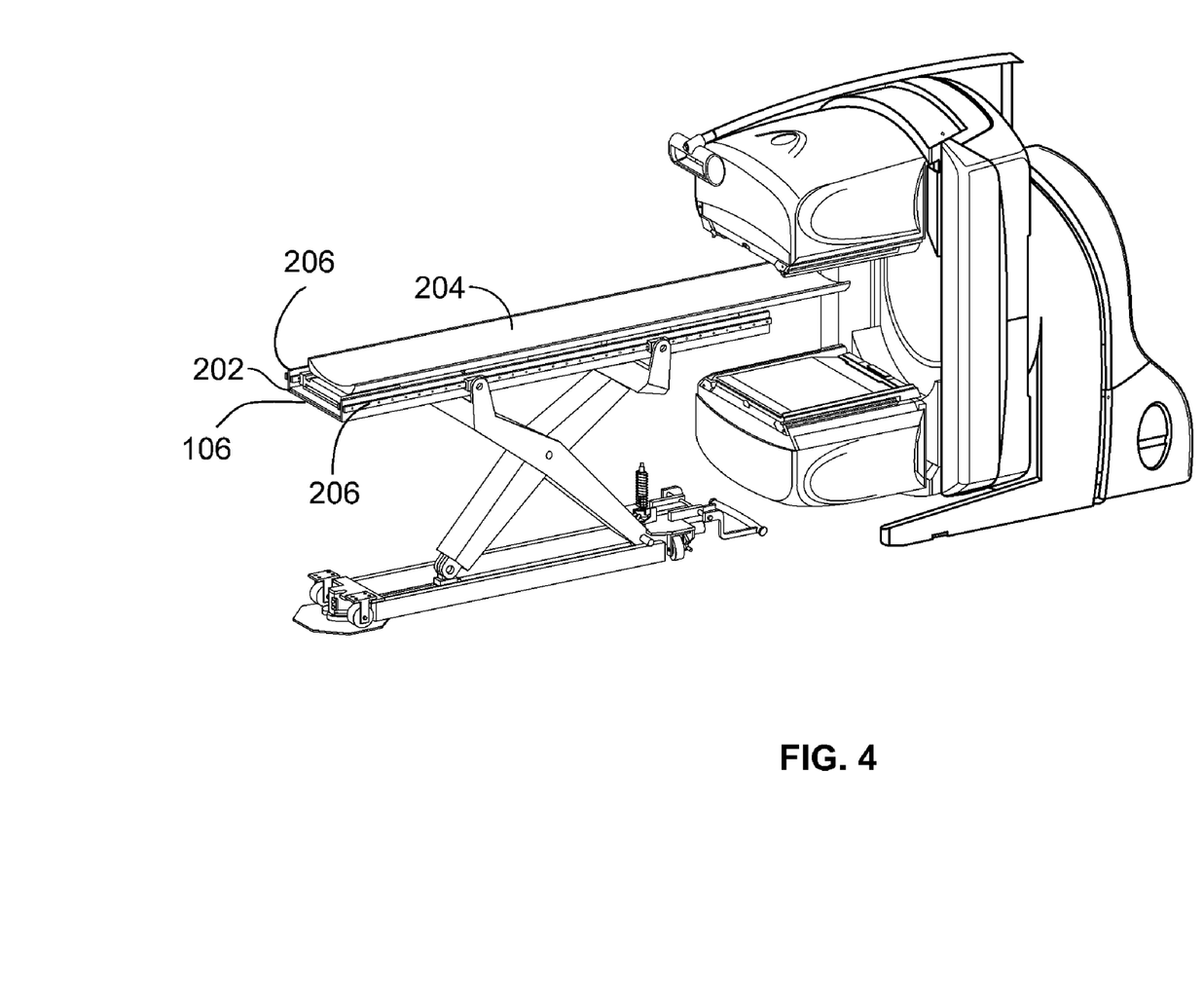
FIG. 4 is the patient table of FIG. 2 in position to conduct patient imaging using a first imaging modality.

FIG. 4 illustrates a second axial position of table assembly 106, different from that shown in FIG. 3, in which a patient (not shown) on table assembly 106 is moved from the axial position in FIG. 3 to that shown in FIG. 4. Table assembly 106 is positioned axially by sliding, in unison, top rails 206, top plate 202, and stretcher 204. Sliding motion is along guide pins 208. Axial location of table assembly 106 is selected such that stretcher 204 may be positioned axially, with patient (not shown) positionable such that the region of interest (ROI) for scanning of the patient may be placed in an axial location which can be scanned by first imaging modality 102.

Figure 5:
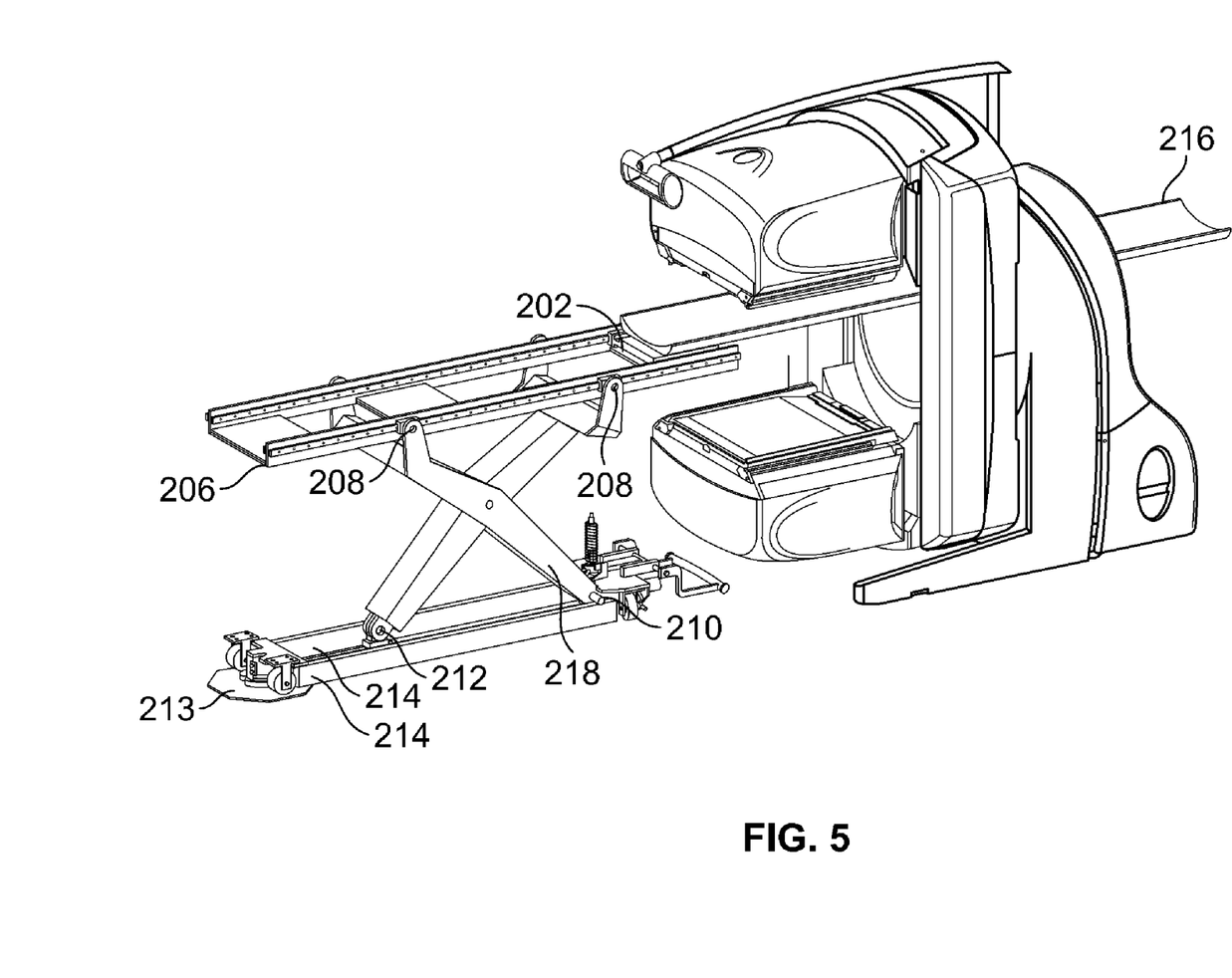
FIG. 5 is the patient table of FIG. 2 in position to conduct patient imaging using a second imaging modality.

FIG. 5 illustrates a range of travel of stretcher 204 in the region of a first imaging modality 102. Top plate 202 is attached to stretcher 204 and both move in unison, guided by top rails 206 which are slideably engaged with top plate 202. Patient imaging in the axial region of first imaging modality 102 is accomplished by slideably engaging top plate 202 while a patient lies on stretcher 204. Notably, during imaging of the patient in the region of first imaging modality 102, imaging is accomplished by relative motion of top plate 202 and top rails 206 and top rails (206) remain substantially stationary.

Figure 6:
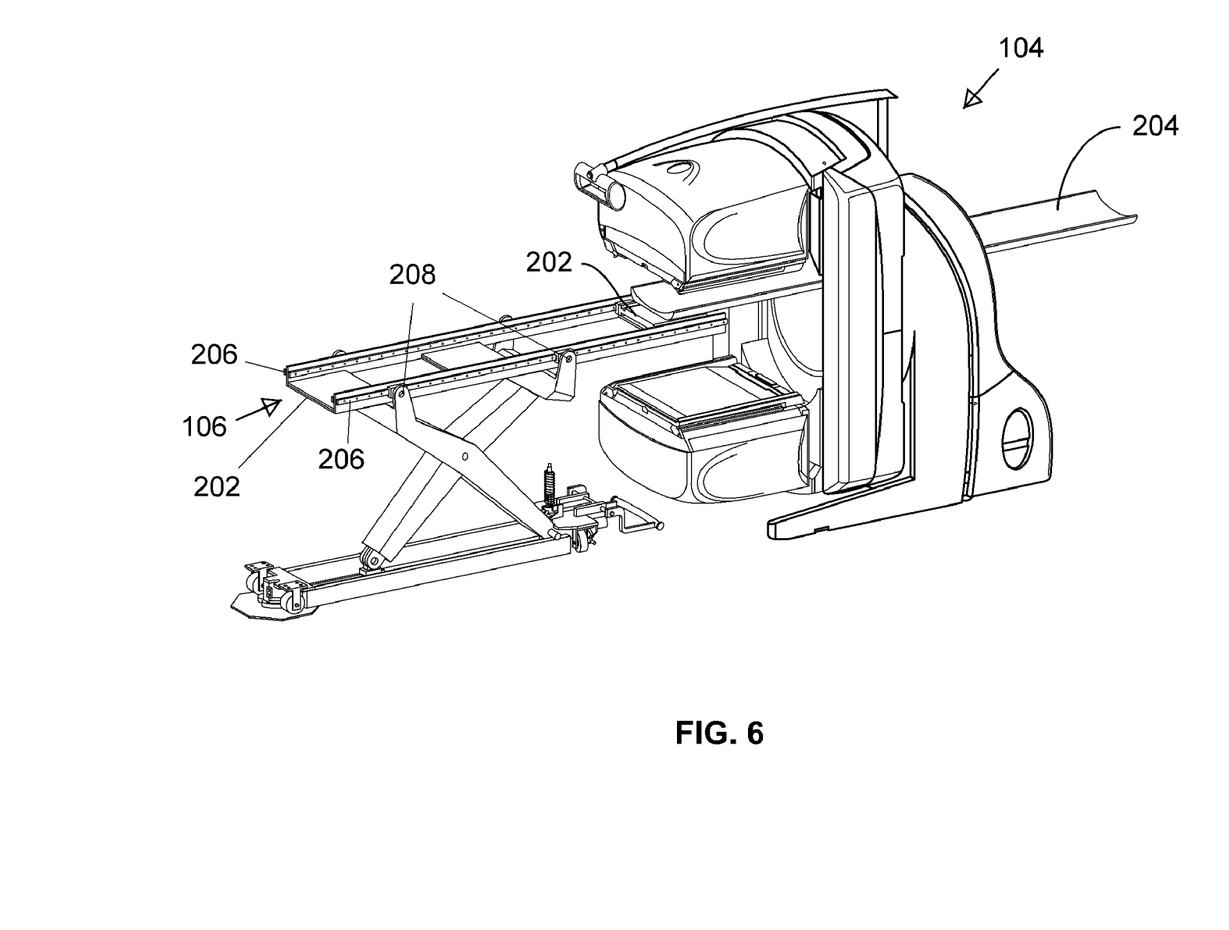
FIG. 6 illustrates a range of travel of the patient table shown in FIG. 2.

FIG. 6 illustrates a range of travel of stretcher 204 in the region of the second imaging modality 104. Top rails 206, top plate 202, and stretcher 204 are moved in unison by slideably engaging top rails 206 through guide pins 208. Stretcher 204 is preferably fabricated from high rigidity material such as carbon fiber reinforced plastic and the like, and stretcher 204 cross section is designed to maximize its second moment of inertia. As such the sag of the patient on table assembly 106 is minimized. Stretcher 204 material is preferably substantially transparent to the passage of x-rays. Accordingly, because the gravitational sag of the patient and table assembly 106 is dominated by the mechanical characteristics of stretcher 204, the gravitational sag is substantially the same for the configurations illustrated in both FIG. 5 and FIG. 6. Having substantially the same sag in both axial locations, a patient will have substantially the same orientational characteristics when positioned for imaging at both the first imaging modality 102 and the second imaging modality 104. Simple translation of table assembly 106 and patient results in substantially the same gravitational sag, hence reconciliation of results from both imaging modalities is simplified.

It is contemplated that the various embodiments of the invention may be implemented with any multi-modality imaging systems, such as, for example, but not limited to, a CT/SPECT imaging system as well as systems having currently known or later developed modalities as well as combinations, such as, for example, but not limited to, a combination SPECT/ultrasound system, a CT/MRI system, and/or a CT/NM system.

The above-described embodiments of multi-modality imaging systems provide a cost-effective and reliable means for examining a patient. Specifically, a patient may be positioned for diagnostic imaging by a first modality, then translated substantially along the imaging axis to a second imaging modality, wherein the gravitational sag of the patient is substantially the same at both axial locations. Accordingly, the multi-modality imaging systems described above provide for maintaining an accurate registration of images from separate modalities in a cost effective and reliable manner.

An exemplary embodiment of a multi-modality imaging system is described above in detail. The multi-modality imaging system components illustrated are not limited to the specific embodiments described herein, but rather, components of each multi-modality imaging system may be utilized independently and separately from other components described herein. For example, the multi-modality imaging system components described above also may be used in combination with other imaging systems.

While the invention has been described in terms of various specific embodiments, those skilled in the art will recognize that the invention can be practiced with modification within the spirit and scope of the claims.

What is claimed is:

1. A method of examining a patient, said method comprising:

aligning a pair of rails, a top plate movably coupled to the pair of rails, and a stretcher coupled to the top plate along an examination axis;

positioning the stretcher and top plate axially at a first imaging modality position by moving the stretcher and top plate along the pair of rails with the pair of rails locked in position relative to a base unit coupled to the pair of rails, wherein the stretcher and top plate are capable of sliding along said examination axis in both directions relative to the base unit;

imaging the patient using a first imaging modality unit;

moving the stretcher, the top plate, and the pair of rails axially along the examination axis until at least a portion of the stretcher and top plate are positioned at a second imaging modality position, wherein the pair of rails are capable of sliding along said examination axis in both directions relative to the base unit, wherein the first imaging modality position is at an axial distance displaced along the examination axis and the second imaging modality position is at a greater displaced distance in the axial direction along the examination axis than the first imaging modality position and a gravitational sag is substantially the same at the first and second imaging modality positions; and imaging the patient using a second imaging modality unit.

2. A method in accordance with claim 1 wherein the stretcher is raised and lowered above a rail using a scissors linkage that is coupled between a support member and the rail, the linkage having scissors legs configured to pivot about a pivot axis.

\* \* \* \* \*